United States Patent
Hauger et al.

[19]

[11] Patent Number: 5,848,449
[45] Date of Patent: Dec. 15, 1998

[54] SLIDE LOCK DEVICE AND METHOD FOR SECURING A PATIENT POSITIONING MOLD

[75] Inventors: Todd M. Hauger; Loren G. Kamstra, both of Orange City, Iowa

[73] Assignee: Biotek, Orange City, Iowa

[21] Appl. No.: 851,371

[22] Filed: May 5, 1997

[51] Int. Cl.[6] ....................................................... A61B 6/04
[52] U.S. Cl. ...................... 5/637; 5/601; 5/630; 128/869; 248/316.4; 292/302
[58] Field of Search ................................. 5/601, 630, 632, 5/637, 640, 643, 647, 650; 128/869, 877, 878, 879, 880, 881, 882; 600/407; 248/316.1, 316.4, 500, 118; 403/321, 353, 373; 292/300, 302; 411/522, 523, 524

[56] References Cited

U.S. PATENT DOCUMENTS

| | | | |
|---|---|---|---|
| 1,878,413 | 9/1932 | Leberman | 292/145 |
| 3,145,397 | 8/1964 | Liftman | 5/650 X |
| 3,186,197 | 6/1965 | Gehrie | 292/302 X |
| 3,984,191 | 10/1976 | Doty | 411/522 X |
| 4,283,038 | 8/1981 | Kurtz | 248/316.4 X |
| 4,576,307 | 3/1986 | Frydenberg | 292/302 X |
| 4,979,519 | 12/1990 | Chavarria et al. | 5/637 X |
| 5,370,117 | 12/1994 | McLaurin, Jr. | 5/637 X |
| 5,775,337 | 7/1998 | Hauger et al. | 128/869 |

*Primary Examiner*—Michael F. Trettel
*Assistant Examiner*—Robert G. Santos
*Attorney, Agent, or Firm*—Zarley, McKee, Thomte, Voorhees & Sease

[57] ABSTRACT

A slide lock device is provided for releasably locking a patient positioning mold to a base for accurate and repeatable radiation therapy. The slide lock device includes a rail secured to the base and a tab slidably mounted on the rail for overlapping engagement with the frame of the patient positioning mold. The tab locks the mold against vertical and lateral movement relative to the base in a quick and easy manner. A plurality of holes in the rail allow adjustable positioning of the mold through the use of indexing pins.

13 Claims, 3 Drawing Sheets

SLIDE LOCK DEVICE AND METHOD FOR SECURING A PATIENT POSITIONING MOLD

BACKGROUND OF THE INVENTION

In radiation therapy treatment, it is critical that the patient be positioned accurately for each treatment session. Accurate repeatability for treating the same anatomical area of the patient is necessary for successful treatment.

Patient positioning systems have been developed for indexing the patient in a particular position and restraining the area to be treated. Such systems typically use moldable thermoplastic which sets into a rigid mold that extends over the patient's anatomical area that is to be treated. A moldable vacuum cushion is normally placed under the anatomical area. Different devices have been used to lock the mold onto a base beneath the cushion so as to properly index the patient and so as to restrain the patient from moving the area to be treated. Typically, at least four locking devices are provided at four spaced apart anchor points so as to securely lock the mold to the base.

One type of prior art locking device is a thumb screw extending through the mold and into a threaded indexing hole in the base. Each thumb screw must be hand tightened for locking the mold onto the base and hand loosened for removal of the mold from the base. Use of such a thumb screw device is slow and time consuming.

Another type of locking device is a push-pin system wherein a pin extends downwardly from the mold for insertion into an indexing hole in the base. The diameter of the pin expands with downward force so as to lock the mold to the base plate. However, upward pressure exerted by the patient can pull the locking push-pin from the indexing hole.

A third type of locking system is a swivel clamp which pivots from a position disengaged from the mold to an overlapping mold-engaging position to prevent the mold from moving upwardly relative to the base. The swivel clamp locking system does not allow for multiple indexing lock points, which are necessary to adjust for various patient sizes.

Accordingly, a primary objective of the present invention is the provision of an improved locking device for patient positioning molds used in radiation therapy.

Another objective of the present invention is the provision of a slide lock device for releasably locking a radiation therapy patient positioning mold to a base.

A further objective of the present invention is the provision of a slide lock device which will quickly and easily secure a patient positioning mold to a base for radiation therapy treatment.

Another objective of the present invention is the provision of a method for releasably locking a radiation therapy patient positioning mold to a base for accurate repeatable radiation therapy of a specific area on a patient's anatomy.

Still another objective of the present invention is the provision of a slide lock device which is economical to manufacture, and durable and safe in use.

These and other objectives will become apparent from the following description of the invention.

SUMMARY OF THE INVENTION

A slide lock device is provided for quickly and easily releasably locking a patient positioning mold to a base for accurate and repeatable radiation therapy treatment. The slide lock device includes a rail attached to the base and a tab slidably mounted on the rail. The tab includes a retainer with a pair of spaced apart fingers spaced upwardly from the rail to define a space between the retainer and the rail. The frame of the mold is adapted to be received in the space, such that the fingers overlappingly engage the mold frame thereby preventing upward movement of the frame relative to the base. An indexing pin on the mold frame has a lower leg selectively positioned in one of a plurality of holes in the rail. The head of the indexing pin is received between the spaced apart fingers of the retainer of the tab, thereby preventing lateral movement of the mold relative to the frame.

In the method for releasably locking the patient positioning mold to the base, the patient is positioned on the base, and the mold is then placed over the portion of the patient's body receiving radiation therapy. The indexing pins in the mold are inserted into corresponding holes on the rails which are securely attached to the base. Each tab is then slid along its rail into overlapping engagement with the mold frame, thereby locking the mold frame into position relative to the base.

DETAILED DESCRIPTION OF THE DRAWINGS

Figures 1, 8, 9, 10:
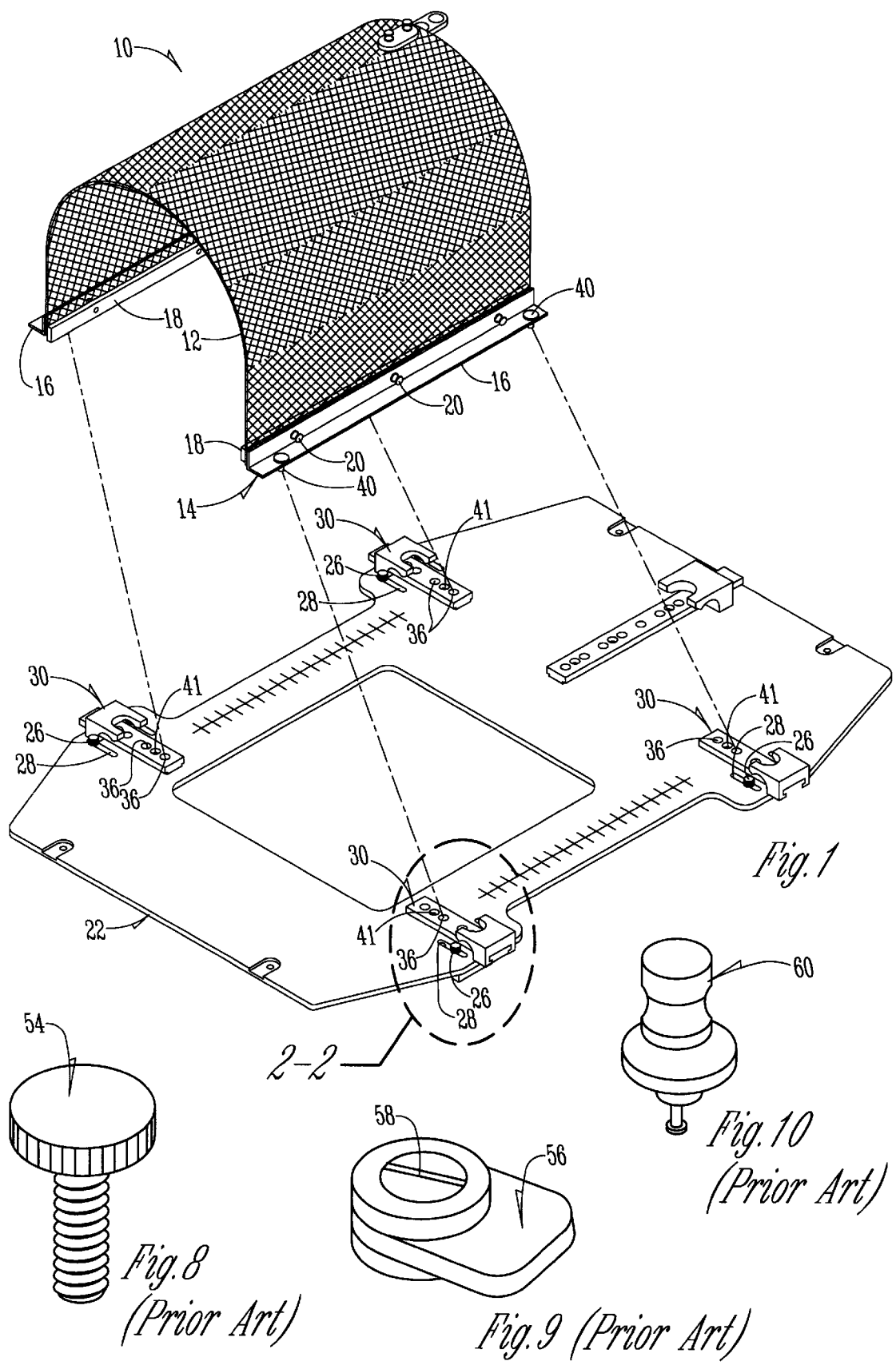
FIG. 1 is an exploded perspective view of a patient positioning mold and a radiation therapy base plate with the slide lock device of the present invention mounted thereon.
FIG. 8 is a perspective view of a prior art thumb screw locking device.
FIG. 9 is a perspective view of a prior art swivel clamp locking device.
FIG. 10 is a perspective view of a prior art push-pin locking device.

With reference to the drawings, a patient positioning mold for use in radiation therapy is generally designated by the reference numeral 10. FIG. 1 shows a mold for the pelvic region of a patient for use in a prone position. The mold 10 generally includes a deformable thermoplastic mesh membrane 12 mounted on frames 14. Each frame 14 includes an outer L-shaped member 16 and a flat inner member 18. The mesh membrane 12 is clamped between the inner and outer frame member 16–18 with screws 20. The mold 10 is conventional and may have a different shape corresponding to the anatomical body part which is to be held against movement during the radiation therapy process.

A conventional base or base plate 22 is normally fixed to a radiation therapy treatment table 24 using any convenient means, such as screws 26. The base 22 may take various forms, as are known in the art. Slots 28 are provided in the base 22 to allow for adjustable positioning of the base 22 relative to the table 24.

The present invention is directed towards a slide lock device 30 used to securely attach the patient positioning mold 10 to the base 22. FIG. 1 shows the base 22 as having five slide lock devices 30, however, more or less locking devices may be utilized. Other than length, each slide locking device 30 is identical in construction and function.

Each slide lock device 30 includes a rail 32 and a tab 34 slidably mounted on the rail 32. The rail 32 includes a plurality of indexing holes 36 adapted to receive the lower leg 38 of an indexing pin 40 on the mold frame 14. The rail 32 is secured to the base 22 by one or more screws 41 extending through screw holes 37. Alternatively, or in addition to the securing screws 41, adhesive may be used to secure the rail 32 to the base 22.

Figure 2:
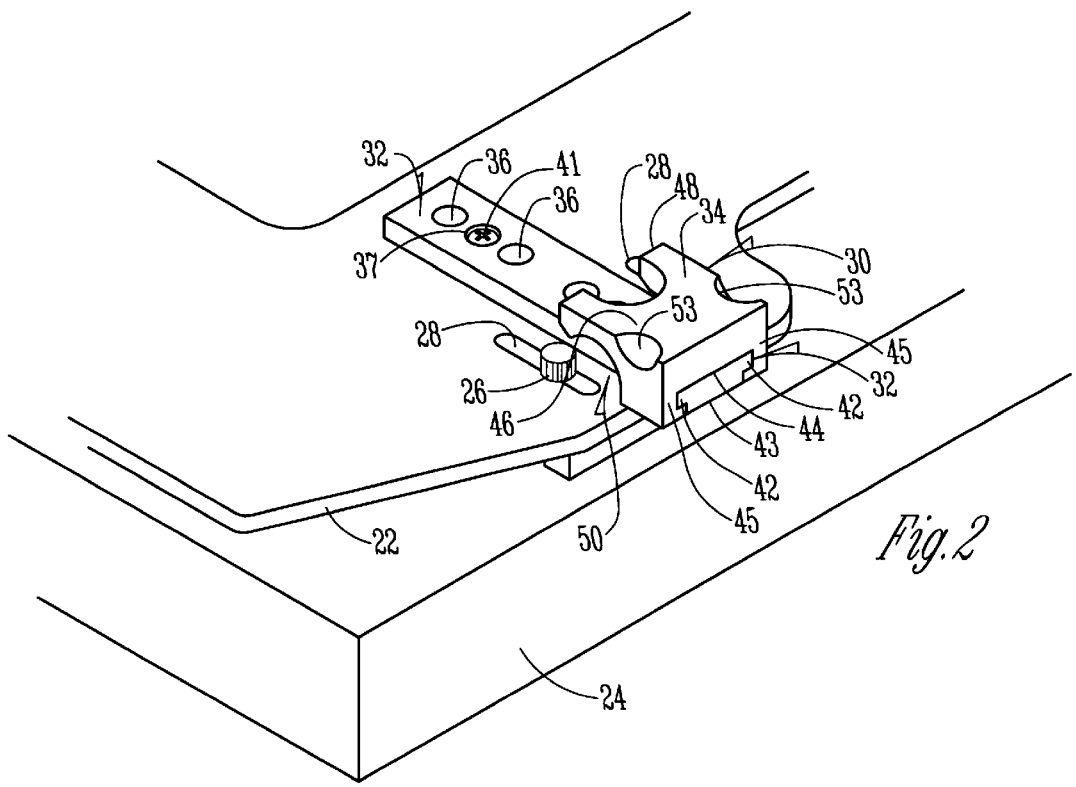
FIG. 2 is an enlarged partial perspective view taken along line 2—2 of FIG. 1.
Figure 3:
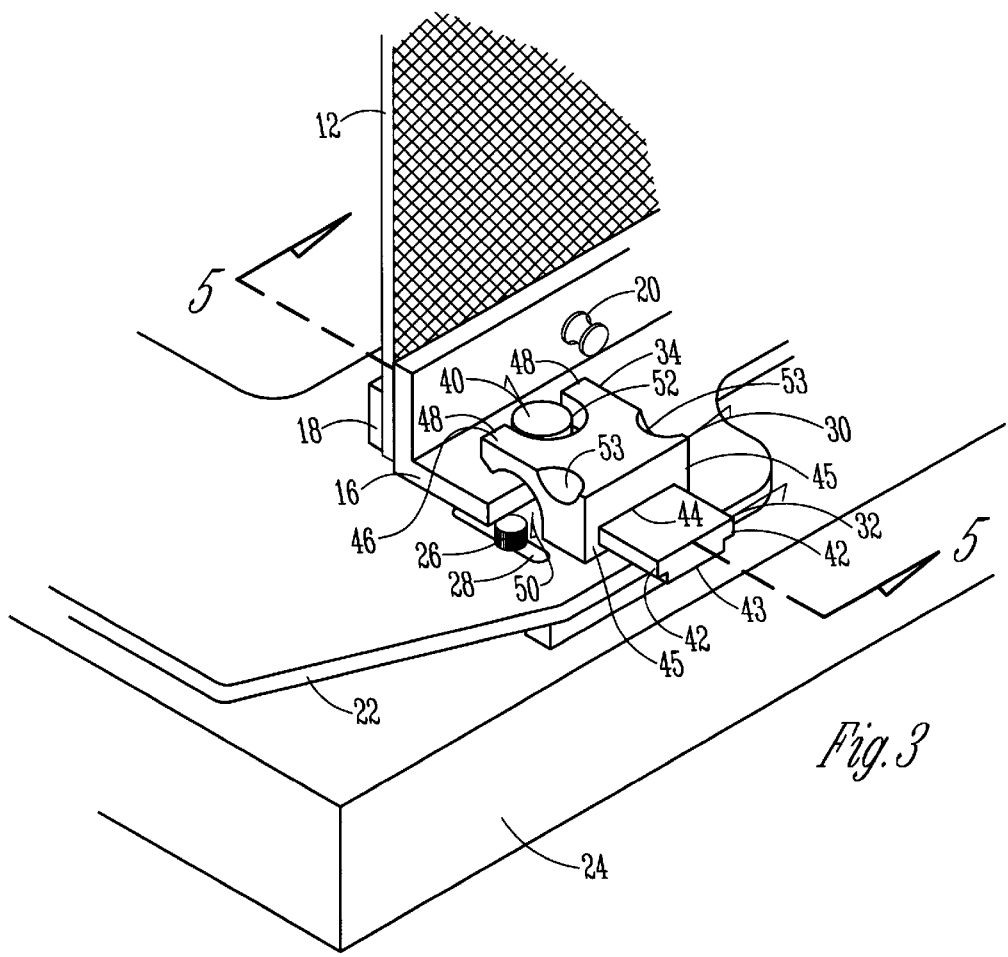
FIG. 3 is a perspective view similar to FIG. 2, showing one corner of the patient mold secured to the base by one of the slide lock devices of the present invention.
Figure 4:
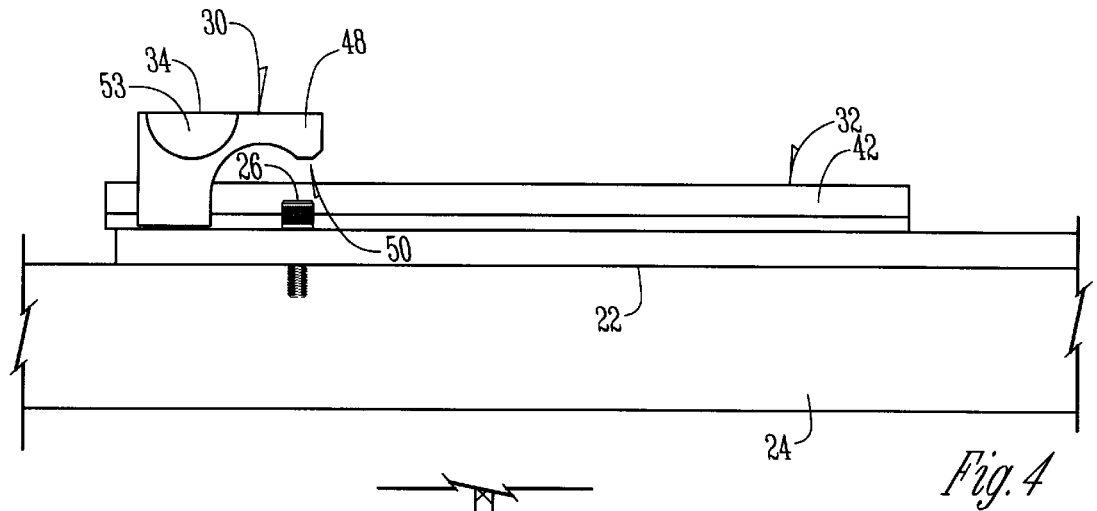
FIG. 4 is a side elevation view of the slide lock device shown in FIG. 2.
Figure 7:
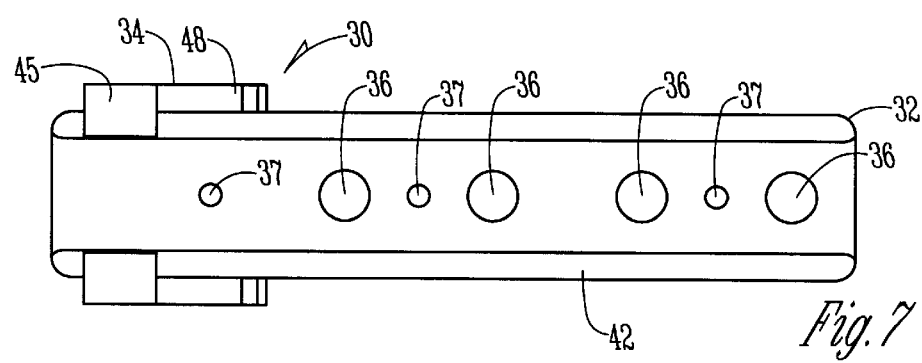
FIG. 7 is a bottom plan view of the device.

As best seen in FIGS. 2 and 3, the rail 32 has a T-shaped cross section so as to have oppositely extending arms 42 and a base 43. The tab 34 is C-shaped in cross sections so as to have a corresponding slot 44 to slidingly receive the rail 32. As seen in FIG. 7, the base 43 of the rail 32 is slightly flared at the opposite ends so that the tab 34 does not slide off of the rail. The legs 45 of the tab 34 are resilient so that the tab can slide over one end of the rail 32 when the rail and the tab are initially assembled.

It is understood that the cross sectional shapes of the rails 32 and the tab 34 may vary from that shown in the drawings. For example, while the drawings show the male rail 32 being received within the female slot 44 of the tab 34, these components can be reversed such that the rail has a female slot for slidably receiving a male portion of the tab.

Figure 5:
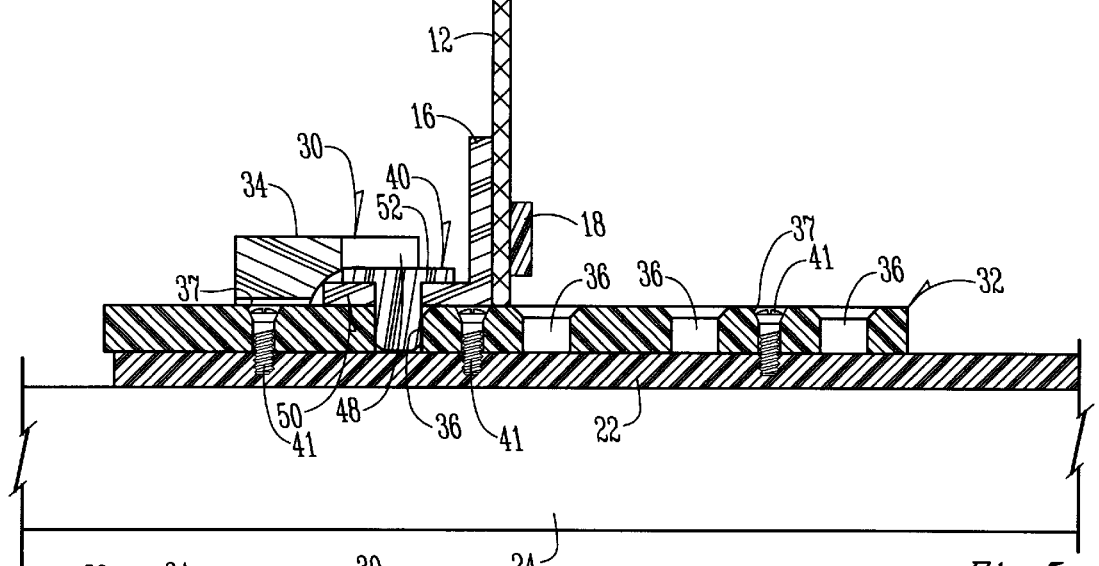
FIG. 5 is a sectional view taken along lines 5—5 of FIG. 3.
Figure 6:
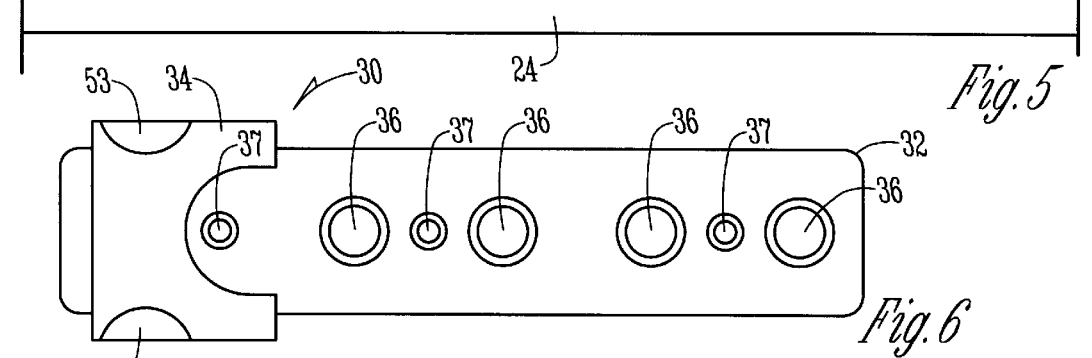
FIG. 6 is a top view of the slide lock device.

Each tab 34 includes a retainer portion 46 which includes a pair of inwardly extending, spaced apart fingers 48. The fingers 48 are spaced upwardly from the rail so as to define a space 50 therebetween adapted to receive the leg of the L-shaped outer frame member 16, as best seen in FIGS. 2 and 5. The space between the opposing fingers 48 is adapted to receive the head 52 of the indexing pin 40, as seen in FIG. 2. Thus, the slide lock device 30 of the present invention locks the mold 10 against upward and lateral movement relative to the base 22.

Preferably, the rail 32 and the tab 34 is made from a plastic material which permits easy sliding movement of the tab 34 along the rail 32. Indentations 53 are provided on the tab 34 for gripping the tab between a user's finger and thumb.

In using the slide lock device of the present invention, the patient is first positioned on the treatment table 24 over the base 22. A positioning cushion (not shown) may be positioned beneath the patient, as is known in the art. The mold 10 is placed over the anatomical portion of the patient's body which is to be restrained against movement during the radiation therapy treatment process. The indexing pins 40 are inserted into the selected holes 36 in the rails 32. The tabs 34 can then be quickly and easily slid into position with the retainer fingers 48 overlappingly engaging the outer mold frame 16, thereby locking the mold frame against movement relative to the base 22. When the treatment is completed, the tab 34 can be quickly and easily slid out of engagement with the frame member 16, such that the mold 10 can be removed and the patient may move from the table 24.

FIGS. 8–10 show prior art locking devices. More particularly, FIG. 8 shows a threaded thumb screw insert 54 which extends through a corresponding hole in the frame of the mold for receipt in a threaded hole in the base. FIG. 9 shows a swivel clamp 56 which is mounted to the base by a screw or bolt 58. The clamp 56 is thus pivotal about the axis of the screw 58 so as to pivot into overlapping engagement with the frame of the mold so as to hold the mold against vertical movement relative to the base. FIG. 10 shows a push-pin 60 which is mounted to the frame of the mold so as to extend downwardly therefrom and into a selected hole on the base. Downward pressure on the push-pin 60 expands its diameter so as to lock the pin in the hole in the base, thereby securing the mold to the base.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. In combination, a base, a radiation therapy patient positioning mold having a frame with an index pin including a downwardly extending leg and an upwardly disposed head, and a device for locking the mold to the base, the device comprising:

a rail secured to the base and having a plurality of holes therein for receiving the leg of the indexing pin;

a tab slidably mounted to the rail and having a retainer spaced upwardly from the rail to define a space for receiving the frame of the mold sandwiched between the retainer and the rail;

the tab being slidable along the rail so as to overlappingly engage the frame of the mold and thereby lock the mold in place on the base.

2. The combination of claim 1 wherein the retainer includes a pair of spaced apart fingers for receiving the head of the indexing pin.

3. The combination of claim 1 wherein the rail is T-shaped in cross-section and the tab includes a slot to slidably fit over the rail.

4. The combination of claim 1 wherein one of the rail and tab has a male portion and the other of the rail and tab has a female portion for slidably receiving the male portion.

5. The combination of claim 1 wherein the rail of the device is directly secured to the base.

6. The combination of claim 1 wherein the rail of the device is rigidly secured to the base.

7. A slide lock device for releasably locking a frame to a base, the frame having an indexing pin with a downwardly extending leg and an upwardly disposed head, the device comprising:

a rail for attachment to the base and having a plurality of holes for receiving the leg of the indexing pin;

a slide tab slidably mounted on the rail for longitudinal movement with respect thereto and having a retainer extending therefrom in spaced relation to the rail for sandwiching the frame between the retainer and the rail and thereby locking the frame to the base.

8. The slide lock device of claim 7 wherein the retainer has a pair of laterally spaced apart fingers adapted to receiving an indexing pin extending through the frame so as to prevent lateral movement of the frame relative to the base.

9. The slide lock device of claim 7 wherein the rail is elongated such that the frame is selectively positionable along the rail for locking engagement by the slide tab.

10. The slide lock device of claim 7 wherein one of the slide tab and rail includes a slot and the other of the slide tab and rail includes an extension slidably receivable in the slot.

11. A method for releasably locking a radiation therapy patient positioning mold to a base for accurate repeatable radiation therapy of a patient, the method comprising:

positioning a patient on the base;

placing the mold over the patient's body;

inserting indexing pins on the mold into corresponding holes in a plurality of rails on the base;

sliding a tab along each rail into overlapping engagement with the mold so as to lock the mold against upward movement relative to the base.

12. The method of claim 11 further comprising positioning spaced apart fingers on the tab on opposite sides of the indexing pin so as to lock the mold against lateral movement relative to the base.

13. The method of claim 11 further comprising disengaging the tab from the mold to release the mold from the base.

* * * * *